(12) United States Patent
Ludwig et al.

(10) Patent No.: US 12,419,560 B2
(45) Date of Patent: Sep. 23, 2025

(54) DRY ELECTRODES

(71) Applicant: Solventum Intellectual Properties Company, Maplewood, MN (US)

(72) Inventors: Bret W. Ludwig, Oakdale, CA (US); Matthew J. Bongers, Minneapolis, MN (US); Audrey A. Sherman, Woodbury, MN (US); Jeffrey A. Wiser, Coon Rapids, MN (US); Jeffrey D. Cotton, St. Paul, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 1091 days.

(21) Appl. No.: 17/292,555

(22) PCT Filed: Oct. 28, 2019

(86) PCT No.: PCT/IB2019/059234
§ 371 (c)(1),
(2) Date: May 10, 2021

(87) PCT Pub. No.: WO2020/099965
PCT Pub. Date: May 22, 2020

(65) Prior Publication Data
US 2022/0000407 A1 Jan. 6, 2022

Related U.S. Application Data

(60) Provisional application No. 62/760,351, filed on Nov. 13, 2018.

(51) Int. Cl.
*A61B 5/24* (2021.01)
*A61B 5/00* (2006.01)
(Continued)

(52) U.S. Cl.
CPC .............. *A61B 5/259* (2021.01); *A61B 5/265* (2021.01); *H01B 5/14* (2013.01); *A61B 2562/125* (2013.01)

(58) Field of Classification Search
CPC ........... A61B 5/291; A61B 5/25; A61B 5/282; A61B 5/296; A61B 2562/0215;
(Continued)

(56) References Cited

U.S. PATENT DOCUMENTS 2,736,721 A   2/1956   Dexter
3,437,622 A   4/1969   Dahl
(Continued)

FOREIGN PATENT DOCUMENTS

CN      106108890     11/2016
WO      WO 1994-007409   4/1994
(Continued)

OTHER PUBLICATIONS

International Search report for PCT International Application No. PCT/IB2019/059234 mailed on Feb. 2, 2020, 6 pages.

*Primary Examiner* — Joseph A Stoklosa
*Assistant Examiner* — Brian M Antiskay (57) ABSTRACT

Dry electrodes are electrodes for attachment to human skin without skin preparation or the use of electrolyte gels. The electrode includes a substrate, electrically conductive particles with at least one point, in contact with the substrate, a supporting layer that envelopes the electrically conductive particles with points that protrude from the supporting layer, and an electrical connector. Some electrodes have an electrically conductive substrate, other electrodes have an electrically conductive supporting layer.

12 Claims, 5 Drawing Sheets

(51) Int. Cl.
*A61B 5/259* (2021.01)
*A61B 5/265* (2021.01)
*H01B 5/14* (2006.01)

(58) Field of Classification Search
CPC ......... A61B 5/259; A61B 5/24; A61B 5/6833; A61B 2562/0217; A61B 2562/125; A61B 2562/164; A61B 5/257; A61B 5/0006; A61B 5/389; A61B 5/266; A61B 2018/00839; A61B 5/28; A61B 5/325; A61B 5/369; A61B 2018/1425; A61B 5/0531; A61B 5/6848; A61B 5/68335; A61N 1/0558; A61N 1/0492; A61N 1/36017; A61N 1/36021; A61N 1/36071
USPC .................. 600/372, 382–395; 607/115–118
See application file for complete search history.

(56) References Cited

U.S. PATENT DOCUMENTS

| | | | |
|---|---|---|---|
| 3,718,712 A | 2/1973 | Tushaus | |
| 3,774,592 A | 11/1973 | Lahr | |
| 3,911,906 A | 10/1975 | Reinhold, Jr. | |
| 4,314,827 A | 2/1982 | Leitheiser | |
| 4,554,324 A | 11/1985 | Husman | |
| 4,612,242 A | 9/1986 | Vesley | |
| 4,737,559 A | 4/1988 | Kellen | |
| 4,744,802 A | 5/1988 | Schwabel | |
| 5,197,471 A * | 3/1993 | Otero | A61B 5/25 600/394 |
| 5,209,971 A | 5/1993 | Babu | |
| 5,214,119 A | 5/1993 | Leir | |
| 5,309,909 A * | 5/1994 | Gadsby | A61B 5/274 600/394 |
| 5,506,279 A | 4/1996 | Babu | |
| 5,551,963 A | 9/1996 | Larmie | |
| 5,591,820 A | 1/1997 | Kydonieus | |
| 5,645,619 A | 7/1997 | Erickson | |
| 6,083,856 A | 7/2000 | Joseph | |
| 6,277,161 B1 | 8/2001 | Castro | |
| 6,415,170 B1 | 7/2002 | Loutis | |
| 6,622,035 B1 * | 9/2003 | Merilainen | A61B 5/325 607/152 |
| 7,371,464 B2 | 5/2008 | Sherman | |
| 7,727,931 B2 | 6/2010 | Brey | |
| 7,981,995 B2 | 7/2011 | Hays | |
| 8,142,531 B2 | 3/2012 | Adefris | |
| 9,192,313 B1 | 11/2015 | Lisy | |
| 2003/0050550 A1 | 3/2003 | Schmidt | |
| 2004/0204658 A1 * | 10/2004 | Dietz | A61B 5/325 600/547 |
| 2006/0047194 A1 | 3/2006 | Grigorov | |
| 2006/0173261 A1 | 8/2006 | Kall | |
| 2011/0130640 A1 * | 6/2011 | Dunagan | A61B 5/6804 600/388 |
| 2013/0325096 A1 * | 12/2013 | Dupelle | A61N 1/0496 607/142 |
| 2014/0275897 A1 * | 9/2014 | Pushpala | A61B 5/150984 600/347 |
| 2014/0363554 A1 | 12/2014 | Hajime | |
| 2015/0238100 A1 | 8/2015 | Lin | |
| 2017/0323698 A1 * | 11/2017 | Hatakeyama | A61B 5/259 |
| 2017/0340226 A1 | 11/2017 | Takagahara | |
| 2018/0017715 A1 | 1/2018 | Matsuda | |

FOREIGN PATENT DOCUMENTS

| | | |
|---|---|---|
| WO | WO 1999-042536 | 8/1999 |
| WO | WO 2000-075210 | 12/2000 |
| WO | WO 2015-143443 | 9/2015 |
| WO | WO 2017-112394 | 6/2017 |

* cited by examiner

DRY ELECTRODES

FIELD OF THE DISCLOSURE

This disclosure relates generally to dry electrodes, electrodes for attachment to human skin without skin preparation or the use of electrolyte gels, and methods for preparing these dry electrodes.

BACKGROUND

Electrodes for measuring biopotential are used extensively in modern clinical and biomedical applications. The applications encompass numerous physiological tests including electrocardiography (ECG), electroencephalography (EEG), electrical impedance tomography (EIT), electromyography (EMG), and electro-oculography (EOG). The electrodes for these types of physiological tests function as a transducer by transforming the electric potential or biopotentials within the body into an electric voltage that can be measured by conventional measurement and recording devices.

SUMMARY

The present disclosure relates to dry electrodes, electrodes for attachment to human skin without skin preparation or the use of electrolyte gels. Disclosed herein are dry electrodes, sheet article precursors for preparing dry electrodes, and methods for preparing these dry electrodes.

In some embodiments, the electrode comprises an electrically conductive substrate with a first major surface and a second major surface, a discontinuous layer of electrically conductive particles, at least some of the electrically conductive particles are in contact with the second major surface of the conductive substrate, and comprise shaped particles with at least one point. The electrode also comprises a supporting layer with a first major surface and a second major surface, where the first major surface of the supporting layer is in contact with the second major surface of the electrically conductive substrate and the supporting layer envelopes the electrically conductive particles such that the at least one point of at least one of the electrically conductive particles protrudes from the second major surface of the supporting layer. Also included in the electrode is an electrical connector in electrical contact with the second major surface of the electrically conductive substrate, and protruding from the electrically conductive substrate.

In other embodiments, the electrode comprises an electrically conductive substrate with a first major surface and a second major surface, a discontinuous layer of electrically conductive particles wherein at least some of the electrically conductive particles comprise shaped particles with at least one point and the electrically conductive substrate envelopes the electrically conductive particles such that the at least one point of at least one of the electrically conductive particles protrudes from the second major surface of the electrically conductive substrate, and an electrical connector in electrical contact with the second major surface of the electrically conductive substrate, the electrically conductive particles, or a combination thereof. The electrical connector protrudes from the electrically conductive substrate.

In yet another embodiment, the dry electrode comprises an electrical connector with a second major surface comprising an electrode plate portion and a first major portion comprising a head portion, and a discontinuous layer of electrically conductive particles in electrical contact with the second major portion of the electrical connector, and wherein the electrically conductive particles comprise shaped particles with at least one point.

Also disclosed are sheet articles that can be precursors to dry electrodes. In some embodiments, the sheet article comprises a substrate with a first major surface and a second major surface, a discontinuous layer of electrically conductive particles, at least some of the electrically conductive particles are in contact with the second major surface of the substrate, and the electrically conductive particles comprise shaped particles with at least one point. The sheet article also comprises a supporting layer with a first major surface and a second major surface, where the first major surface of the supporting layer is in contact with the second major surface of the substrate and the supporting layer envelopes the electrically conductive particles such that the at least one point of at least one of the electrically conductive particles protrudes from the second major surface of the supporting layer. In some embodiments, the substrate comprises an electrically conductive layer. In other embodiments, the supporting layer comprises an electrically conductive layer, and the substrate comprises a non-conductive substrate.

Also disclosed are methods for preparing a dry electrode. In some the embodiments, the method comprises preparing a precursor sheet article, where preparing the precursor sheet article comprises providing a substrate with a first major surface or a second major surface, providing electrically conductive particles, the electrically conductive particles comprise shaped particles with at least one point, contacting at least one electrically conductive particle with the second major surface of the substrate such that the at least one point protrudes from the second major surface of the substrate, providing a layer of supporting material with a first major surface and a second major surface, contacting the first major surface of the layer of supporting material to the second major surface of the substrate and the electrically conductive particles, such that the at least one point of at least one electrically conductive particle protrudes through the second major surface of the supporting material layer. The method further comprises contacting an electrical connector to the electrically conductive substrate to form electrical connectivity. In some embodiments, the substrate comprises an electrically conductive substrate. In other embodiments, the substrate comprises a non-conductive substrate and the layer of supporting material comprises an electrically conductive layer.

BRIEF DESCRIPTION OF THE DRAWINGS

The present application may be more completely understood in consideration of the following detailed description of various embodiments of the disclosure in connection with the accompanying drawings.

In the following description of the illustrated embodiments, reference is made to the accompanying drawings, in which is shown by way of illustration, various embodiments in which the disclosure may be practiced. It is to be understood that the embodiments may be utilized and structural changes may be made without departing from the scope of the present disclosure. The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Electrodes for measuring biopotential are used extensively in modern clinical and biomedical applications. The applications encompass numerous physiological tests including electrocardiography (ECG), electroencephalography (EEG), electrical impedance tomography (EIT), electromyography (EMG), and electro-oculography (EOG). The electrodes for these types of physiological tests function as a transducer by transforming the electric potential or biopotentials within the body into an electric voltage that can be measured by conventional measurement and recording devices.

In general, such electrodes are attached to the surface of the skin. A difficulty with electrodes placed on the surface of the skin is that the outer layer of skin, the stratum corneum, lacks moisture, and this lack of moisture gives high impedance. This high impedance results from the lack of ion mobility due to the lack of moisture in the stratum corneum.

Electrical conduction in the body is based on the movement of ions rather than the movement of electrons as found in metallic conductors. In order to register an electronic signal from the body an electrode must transform ionic conduction to electronic conduction. The vast majority of electrodes available today achieve this transduction through the use of silver/silver chloride reduction/oxidation reactions. A hydrogel containing $Ag^+$ and $Cl^-$ ions adjacent to the skin wets the stratum corneum and enables ion mobility between the skin and the electrode. Transduction occurs within the electrode at the interface of the hydrogel and an electronically conducting material (typically a metal snap or layer of conductive carbon composite). The conducting material is coated with silver, enabling the following reversible reactions and thus the detection of electrical pulses within the body.

One difficulty with the use of hydrogel-containing electrodes is that the water in the hydrogel is subject to evaporation. Therefore, when in use the hydrogel can lose water and become ineffective. Additionally, the loss of water from the hydrogel as the electrode is stored and transported is a significant challenge. In order to prevent water loss from the hydrogel prior to its use, often expensive packaging, such as foil-lined envelopes, are used to increase the limited shelf life of such electrodes.

Therefore, considerable effort has been expended to the development of "dry" electrodes that do not utilize hydrogels. To make dry electrodes, many attempts have focused on an alternative to using a hydrogel to hydrate the dry stratum corneum, which is to use small structures to penetrate the stratum corneum and access the more moisture-rich layers of skin that lie beneath. Generally, the structures are coated with materials that will form a reduction/oxidation couple (typically silver and silver chloride) when in the presence of moisture. Examples of such small structures that have been used include microneedles or similar small, pointed structures to penetrate the stratum corneum to deeper layers of the skin with more moisture where ions are more mobile, enabling conduction.

The methods of manufacturing these electrodes, typically involve injection molding or other similar processes with subsequent coating of the formed microneedle structures with the redox couple are labor intensive, relatively high cost processes. These manufacturing issues have limited dry electrodes to niche markets. Therefore, new processes for preparing dry electrodes in an economical way to permit these electrodes to compete in the marketplace with the relatively easily produced wet electrodes are needed.

In this disclosure, methods of producing dry electrodes are described which involve the use of microreplicated particles that can be prepared in a continuous process. Such particles have been prepared for use in abrasive articles and can be utilized to form skin-penetrating structures in an electrode construction. Further, these particles can be coated with the redox materials in bulk processes. These coated particles are then coated onto conductive substrates to form dry electrodes. The formed dry electrodes as well as the methods of preparing the dry electrodes are described in greater detail below.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. For example, reference to "a layer" encompasses embodiments having one, two or more layers. As used in this specification and the appended claims, the term "or" is generally employed in its sense including "and/or" unless the content clearly dictates otherwise.

The term "adhesive" as used herein refers to polymeric compositions useful to adhere together two adherends. Examples of adhesives are pressure sensitive adhesives and gel adhesives.

Pressure sensitive adhesive compositions are well known to those of ordinary skill in the art to possess properties including the following: (1) aggressive and permanent tack, (2) adherence with no more than finger pressure, (3) sufficient ability to hold onto an adherend, and (4) sufficient cohesive strength to be cleanly removable from the adherend. Materials that have been found to function well as pressure sensitive adhesives are polymers designed and formulated to exhibit the requisite viscoelastic properties resulting in a desired balance of tack, peel adhesion, and shear holding power. Obtaining the proper balance of properties is not a simple process.

As used herein, the term "gel adhesive" refers to a tacky semi-solid crosslinked matrix containing a liquid or a fluid that is capable of adhering to one or more substrates. The gel adhesives may have some properties in common with pressure sensitive adhesives, but they are not pressure sensitive adhesives. "Hydrogel adhesives" are gel adhesives that have water as the fluid contained within the crosslinked matrix.

The term "(meth)acrylate" refers to monomeric acrylic or methacrylic esters of alcohols. Acrylate and methacrylate monomers or oligomers are referred to collectively herein as "(meth)acrylates". Materials referred to as "(meth)acrylate functional" are materials that contain one or more (meth) acrylate groups.

As used herein, the terms "shaped abrasive particle" and "shaped particle" are used interchangeably, and refer to ceramic particles that can be used as abrasive particles with at least a portion of the particle having a predetermined shape that is replicated from a mold cavity used to form the shaped precursor particle. The shaped particle will generally have a predetermined geometric shape that substantially replicates the mold cavity that was used to form the shaped particle. Shaped particles as used herein excludes abrasive particles obtained by a mechanical crushing operation.

The terms "room temperature" and "ambient temperature" are used interchangeably to mean temperatures in the range of 20° C. to 25° C.

The terms "Tg" and "glass transition temperature" are used interchangeably. If measured, Tg values are determined by Differential Scanning calorimetry (DSC) at a scan rate of 10° C./minute, unless otherwise indicated. Typically, Tg values for copolymers are not measured but are calculated using the well-known Fox Equation, using the monomer Tg values provided by the monomer supplier, as is understood by one of skill in the art.

Disclosed herein are sheet articles that can be used to make dry electrodes, dry electrodes, and methods of making dry electrodes. The sheet articles, described herein are essentially continuous sheets that contain multiple layers of polymeric and non-polymeric materials, where the polymeric and non-polymeric layers may be continuous or discontinuous. An advantage of preparing sheet articles that can be then cut, formed or shaped into dry electrodes is the versatility and low cost of such processes relative to the other options available for making dry electrodes. A wide range of dry electrodes can be prepared using the sheet articles of this disclosure. Additionally, as will be described in greater detail below, the use of electrically conductive shaped particles permits the direct formation of discrete dry electrodes as well as the dry electrodes formed from the sheet articles of this disclosure. Additionally, the discrete dry electrodes can be formed in an array, and thereby again take advantage of low cost manufacturing processes.

A wide variety of sheet articles can be prepared and used to form dry electrodes. In general, the sheet articles comprise a substrate layer, a supporting layer, with a discontinuous layer of conductive particles surrounded by the supporting layer with at least one point of the conductive particles protruding from the supporting layer. A wide range of materials can be used to prepare the sheet articles of this disclosure.

The sheet articles include a substrate layer. This substrate layer functions as a base upon which the remainder of the sheet material can be assembled. A wide range of substrate layers are suitable. In some embodiments, the substrate layer is a single layer, in other embodiments the substrate layer is a multi-layer substrate.

In some embodiments, the substrate layer is a carrier layer, by which it is meant that the substrate layer is used in the preparation of the sheet article, but is not included as a permanent part of the sheet article but rather is removed at some point. Examples of suitable carrier layers include a wide range of polymeric films. In some embodiments, the substrate layer comprises a release liner. Release liners are well understood in the adhesive arts and comprise a polymeric film which either has inherent release properties or has a release coating on at least one surface.

In some embodiments, the substrate comprises a non-conductive substrate like the carrier layers described above, but the substrate is not removed from the electrode. In this way the non-conductive substrate remains in the final article.

In other embodiments, the substrate comprises an electrically conductive substrate with a first major surface and a second major surface. The electrically conductive substrate may comprise a single layer construction or it may be a multi-layer construction. If the electrically conductive substrate is a multi-layer construction, the second major surface of the multi-layer construction is a conductive layer, such that the conductive particles are in electrical contact with the conductive layer. In some embodiments, the electrically conductive substrate comprises a two-layer construction with a conductive layer and a non-conductive layer. A wide range of such electrically conductive substrates are suitable. In some embodiments, the electrically conductive substrate comprises a film layer, such as a polymeric film layer, with a conductive coating. Examples of polymeric films include films comprising one or more polymers such as cellulose acetate butyrate; cellulose acetate propionate; cellulose tri-acetate; poly(meth)acrylates such as polymethyl methacrylate; polyesters such as polyethylene terephthalate, and polyethylene naphthalate; copolymers or blends based on naphthalene dicarboxylic acids; polyether sulfones; polyurethanes; polycarbonates; polyvinyl chloride; syndiotactic polystyrene; cyclic olefin copolymers; and polyolefins including polyethylene and polypropylene such as cast and biaxially oriented polypropylene. The film may comprise single or multiple layers, such as polyethylene-coated polyethylene terephthalate. A wide range of conductive coatings are suitable such as thin coatings of metal, metal grids or continuous coatings of conductive carbon.

The sheet articles of this disclosure also include a discontinuous layer of electrically conductive particles. By discontinuous layer it is meant that the layer includes discrete particles that are not all in contact with each other.

A wide variety of electrically conductive particles are suitable for use in the sheet articles of this disclosure. Generally, the electrically conductive particles comprise non-compressive shaped particles with a conductive metal coating. Typically, the conductive particles are prepared from particles prepared by methods used to make shaped abrasive particles, but the conductive particles can have a wide variety of shapes including shapes such as a caltrops. The conductive metal coating may be a multi-layer coating, for example a conductive metal coating may cover the entire or essentially the entire surface of the shaped particles, and a secondary coating, such as a silver coating or a silver/silver chloride coating, may be selectively coated over all or a portion of the first conductive metal coating. In some embodiments, the electrically conductive particles comprise particles that are entirely coated with silver, and a portion of this coating is converted to a silver/silver chloride coating or a portion of the silver coating could be overcoated with a silver chloride coating. In other embodiments, the particles are entirely coated with a conductive coating and a portion of the particles are then coated with silver and converted to a silver/silver chloride coating. While a wide range of sizes and shapes are suitable for the shaped particles, at least one dimension of the shaped particles is 100-1,500 micrometers.

In some embodiments, the non-compressive shaped particles comprise ceramic shaped particles. Examples of suitable ceramic shaped particles are shaped abrasive particles with a sloping sidewall as described in U.S. Pat. No. 8,142,531. The steps of making the shaped particles are described below. Shaped abrasive particles are particularly desirable for use in forming the articles of this disclosure since they can be mass produced with known technologies and coated with an electrically conductive coating to form particles with at least one point. These pointed, electrically conductive particles, when formed into a dry electrode, are non-compressive and are capable of penetrating the stratum corneum.

The first process step involves providing either a seeded or un-seeded dispersion that can be converted into alpha alumina. The alpha alumina precursor composition often comprises a liquid that is a volatile component. The dispersion typically comprises a sufficient amount of liquid for the viscosity of the dispersion to be sufficiently low to enable filling the mold cavities and replicating the mold surfaces, but not so much liquid as to cause subsequent removal of the liquid from the mold cavity to be prohibitively expensive. Boehmite or other aluminum oxide hydrates other than boehmite can be used. Boehmite can be prepared by known techniques or can be obtained commercially. Examples of commercially available boehmite include products having the trademarks "DISPERAL", and "DISPAL", both available from Sasol North America, Inc. or "HiQ-40" available from BASF Corporation. The dispersion may contain a modifying additive or precursor of a modifying additive. The modifying additive can function to enhance some desirable property of the particles or increase the effectiveness of the subsequent sintering step. The dispersion can also contain a nucleating agent to enhance the transformation of hydrated or calcined aluminum oxide to alpha alumina. Nucleating agents suitable for this disclosure include fine particles of alpha alumina, alpha ferric oxide or its precursor, titanium oxides and titanates, chrome oxides, or any other material that will nucleate the transformation. The amount of nucleating agent, if used, should be sufficient to effect the transformation of alpha alumina. Nucleating such dispersions is disclosed in, for example, U.S. Pat. No. 4,744,802 (Schwabel). A peptizing agent can be added to the dispersion to produce a more stable hydrosol or colloidal dispersion. Suitable peptizing agents are monoprotic acids or acid compounds such as acetic acid, hydrochloric acid, formic acid, and nitric acid.

The dispersion can be formed by any suitable means, such as, for example, simply by mixing aluminum oxide monohydrate with water containing a peptizing agent or by forming an aluminum oxide monohydrate slurry to which the peptizing agent is added. Defoamers or other suitable chemicals can be added to reduce the tendency to form bubbles or entrain air while mixing. Additional chemicals such as wetting agents, alcohols, or coupling agents can be added if desired as disclosed in U.S. Pat. No. 5,645,619 (Erickson et al.), U.S. Pat. No. 5,551,963 (Larmie), and U.S. Pat. No. 6,277,161 (Castro).

The second process step involves providing a mold having at least one mold cavity, and generally a plurality of cavities. The plurality of cavities can be formed in a production tool. The production tool can be a belt, a sheet, a continuous web, a coating roll such as a rotogravure roll, a sleeve mounted on a coating roll, or die. The production tool comprises polymeric material. Examples of suitable polymeric materials include thermoplastics such as polyesters, polycarbonates, poly(ether sulfone), poly(methyl methacrylate), polyurethanes, polyvinylchloride, polyolefins, polystyrene, polypropylene, polyethylene or combinations thereof, or thermosetting materials.

The cavity has a specified three-dimensional shape. In an exemplary embodiment, the shape of a cavity can be described as being tetragonal, as viewed from the top, such that the particles formed have a tetrahedral shape. Alternatively, other cavity shapes can be used. The cavities of a given mold can be of the same shape or of different shapes.

The third process step involves filling the cavities in the mold with the dispersion by any conventional technique. In some embodiments, a knife roll coater or vacuum slot die coater can be used. A mold release can be used to aid in removing the particles from the mold if desired.

The fourth process step involves removing the volatile component to dry the dispersion. Desirably, the volatile component is removed by fast evaporation rates. In some embodiments, removal of the volatile component by evaporation occurs at temperatures above the boiling point of the volatile component. An upper limit to the drying temperature often depends on the material the mold is made from. For polypropylene tooling the temperature should be less than the melting point of the plastic.

The fifth process step involves removing the precursor shaped particles from the mold cavities. The precursor shaped particles can be removed from the cavities by using the following processes alone or in combination on the mold: gravity, vibration, ultrasonic vibration, vacuum, or pressurized air to remove the particles from the mold cavities. The precursor particles can be further dried outside of the mold. If the dispersion is dried to the desired level in the mold, this additional drying step is not necessary.

The sixth process step involves calcining the precursor shaped particles. During calcining, essentially all the volatile material is removed, and the various components that were present in the dispersion are transformed into metal oxides. The precursor shaped particles are generally heated to a temperature from 400 to 800° C., and maintained within this temperature range until the free water and over 90 percent by weight of any bound volatile material are removed.

The seventh process step involves sintering the calcined, precursor shaped particles to form alpha alumina particles. Prior to sintering, the calcined, precursor shaped particles are not completely densified and thus lack the desired hardness to be used as shaped particles. Sintering takes place by heating the calcined, precursor shaped particles to a temperature of from 1,000 to 1,650° C. and maintaining them within this temperature range until substantially all of the alpha alumina monohydrate (or equivalent) is converted to alpha alumina and the porosity is reduced to less than 15 percent by volume. The length of time to which the calcined, precursor shaped particles must be exposed to the sintering temperature to achieve this level of conversion depends upon various factors but usually from five seconds to 48 hours is typical. After sintering, the shaped particles can have a Vickers hardness of 10 GPa, 16 GPa, 18 GPa, 20 GPa, or greater.

Other steps can be used to modify the described process, such as rapidly heating the material from the calcining temperature to the sintering temperature, centrifuging the dispersion to remove sludge, waste, etc. Moreover, the process can be modified by combining two or more of the process steps if desired. Conventional process steps that can be used to modify the process of this disclosure are more fully described in U.S. Pat. No. 4,314,827 (Leitheiser).

The above outlined steps are merely illustrative, and the current disclosure is not related to the preparation of non-compressive ceramic particles but rather to their use in a new and unexpected way to prepare sheet articles and dry electrodes.

The formed ceramic particles can be coated with metal using a variety of different techniques. Among the suitable methods are physical vapor deposition. Physical vapor deposition (PVD) describes a variety of vacuum deposition methods which can be used to produce thin films and coatings. PVD is characterized by a process in which the material goes from a condensed phase to a vapor phase and then back to a thin film condensed phase. The most common PVD processes are sputtering and evaporation.

Typically, the ceramic particles are coated with silver using the methods and apparatus described in U.S. Pat. Nos. 4,612,242 and 7,727,931, and US Patent Publication No. 2014/0363554.

The sheet articles also include a supporting layer. The supporting layer has a first major surface and a second major surface. The first major surface of the supporting layer is in contact with the second major surface of the substrate. The supporting layer envelopes the electrically conductive particles such that the at least one point of at least one of the electrically conductive particles protrudes from the second major surface of the supporting layer. Generally, the supporting layer has a thickness of from 25-500 micrometers, in some embodiments 50-150 micrometers.

In some embodiments, the supporting layer comprises a layer of pressure sensitive adhesive. Pressure sensitive adhesives are very suitable supporting layers, as they can function to hold the electrically conductive particles in place and also to adhere the formed dry electrode article to the skin of a user.

A wide range of pressure sensitive adhesives are suitable for use as the supporting layer. Useful pressure sensitive adhesives include those based on natural rubbers, synthetic rubbers, styrene block copolymers, polyvinyl ethers, acrylics, poly-α-olefins, silicones, polyurethanes or polyureas.

Useful natural rubber pressure sensitive adhesives generally contain masticated natural rubber, from 25 parts to 300 parts of one or more tackifying resins to 100 parts of natural rubber, and typically from 0.5 to 2.0 parts of one or more antioxidants. Natural rubber may range in grade from a light pale crepe grade to a darker ribbed smoked sheet and includes such examples as CV-60, a controlled viscosity rubber grade and SMR-5, a ribbed smoked sheet rubber grade.

Tackifying resins used with natural rubbers generally include, but are not limited to, wood rosin and its hydrogenated derivatives; terpene resins of various softening points, and petroleum-based resins, such as, the "ESCOREZ 1300" series of C5 aliphatic olefin-derived resins from Exxon, and "PICCOLYTE S" series, polyterpenes from Hercules, Inc.

Antioxidants are used to retard the oxidative attack on natural rubber, which can result in loss of the cohesive strength of the natural rubber adhesive. Useful antioxidants include, but are not limited to, amines, such as N—N'-di-ß-naphthyl-1,4-phenylenediamine, available as "AGERITE D"; phenolics, such as 2,5-di-(t-amyl) hydroquinone, available as "SANTOVAR A", available from Monsanto Chemical Co., tetrakis[methylene 3-(3',5'-di-tert-butyl-4'-hydroxy-phenyl)propionate]methane, available as "IRGANOX 1010" from Ciba-Geigy Corp., and 2-2'-methylenebis(4-methyl-6-tert butyl phenol), available as Antioxidant 2246; and dithiocarbamates, such as zinc dithiodibutyl carbamate. Other materials can be added to natural rubber adhesives for special purposes, wherein the additives can include plasticizers, pigments, and curing agents to partially vulcanize the pressure sensitive adhesive.

Another useful class of pressure sensitive adhesives are those comprising synthetic rubber. Such adhesives are generally rubbery elastomers, which are either self-tacky or non-tacky and require tackifiers.

Self-tacky synthetic rubber pressure sensitive adhesives include for example, butyl rubber, a copolymer of isobutylene with less than 3 percent isoprene, polyisobutylene, a homopolymer of isoprene, polybutadiene, such as "TAK-TENE 220 BAYER" or styrene/butadiene rubber. Butyl rubber pressure sensitive adhesives often contain an antioxidant such as zinc dibutyldithiocarbamate. Polyisobutylene pressure sensitive adhesives do not usually contain antioxidants. Synthetic rubber pressure sensitive adhesives, which generally require tackifiers, are also generally easier to melt process. They comprise polybutadiene or styrene/butadiene rubber, from 10 parts to 200 parts of a tackifier, and generally from 0.5 to 2.0 parts per 100 parts rubber of an antioxidant such as "IRGANOX 1010". An example of a synthetic rubber is "AMERIPOL 1011A", a styrene/butadiene rubber available from BF Goodrich. Tackifiers that are useful include derivatives of rosins such as "FORAL 85", a stabilized rosin ester from Hercules, Inc., the "SNOWTACK" series of gum rosins from Tenneco, and the "AQUATAC" series of tall oil rosins from Sylvachem; and synthetic hydrocarbon resins such as the "PICCOLYTE A" series, polyterpenes from Hercules, Inc., the "ESCOREZ 1300" series of $C_5$ aliphatic olefin-derived resins, the "ESCOREZ 2000" Series of $C_9$ aromatic/aliphatic olefin-derived resins, and polyaromatic $C_9$ resins, such as the "PICCO 5000" series of aromatic hydrocarbon resins, from Hercules, Inc. Other materials can be added for special purposes, including hydrogenated butyl rubber, pigments, plasticizers, liquid rubbers, such as "VISTANEX LMMH" polyisobutylene liquid rubber available from Exxon, and curing agents to vulcanize the adhesive partially.

Styrene block copolymer pressure sensitive adhesives generally comprise elastomers of the A-B or A-B-A type, where A represents a thermoplastic polystyrene block and B represents a rubbery block of polyisoprene, polybutadiene, or poly(ethylene/butylene), and resins. Examples of the various block copolymers useful in block copolymer pressure sensitive adhesives include linear, radial, star and tapered styrene-isoprene block copolymers such as "KRATON D1107P", available from Shell Chemical Co., and "EUROPRENE SOL TE 9110", available from EniChem Elastomers Americas, Inc.; linear styrene-(ethylene-butylene) block copolymers such as "KRATON G1657", available from Shell Chemical Co.; linear styrene-(ethylene-propylene) block copolymers such as "KRATON G1750X", available from Shell Chemical Co.; and linear, radial, and star styrene-butadiene block copolymers such as "KRATON D1118X", available from Shell Chemical Co., and "EUROPRENE SOL TE 6205", available from EniChem Elastomers Americas, Inc. The polystyrene blocks tend to form domains in the shape of spheroids, cylinders, or plates that causes the block copolymer pressure sensitive adhesives to have two-phase structures. Resins that associate with the rubber phase generally develop tack in the pressure sensitive adhesive. Examples of rubber phase associating resins include aliphatic olefin-derived resins, such as the "ESCOREZ 1300" series and the "WINGTACK" series, available from Goodyear; rosin esters, such as the "FORAL" series and the "STAYBELITE" Ester 10, both available from Hercules, Inc.; hydrogenated hydrocarbons, such as the "ESCOREZ 5000" series, available from Exxon; polyterpenes, such as the "PICCOLYTE A" series; and terpene phenolic resins derived from petroleum or terpentine sources, such as "PICCOFYN A100", available from Hercules, Inc. Resins that associate with the thermoplastic phase tend to stiffen the pressure sensitive adhesive. Thermoplastic phase associating resins include polyaromatics, such as the "PICCO 6000" series of aromatic hydrocarbon resins, available from Hercules, Inc.; coumarone-indene resins, such as the "CUMAR" series, available from Neville; and other high-solubility parameter resins derived from coal tar or petroleum and having softening points above about 85° C., such as the "AMOCO 18" series of alpha-methyl styrene resins, available from Amoco, "PICCOVAR 130" alkyl aromatic polyindene resin, available from Hercules, Inc., and the "PICCOTEX" series of alpha-methyl styrene/vinyl-toluene resins, available from Hercules. Other materials can be added for special purposes, including rubber phase plasticizing hydrocarbon oils, such as, "TUFFLO 6056", available from Lyondell Petrochemical Co., Polybutene-8 from Chevron, "KAYDOL", available from Witco, and "SHELL-FLEX 371", available from Shell Chemical Co.; pigments; antioxidants, such as "IRGANOX 1010" and "IRGANOX 1076", both available from Ciba-Geigy Corp., "BUTAZATE", available from Uniroyal Chemical Co., "CYANOX LDTP", available from American Cyanamid, and "BUTASAN", available from Monsanto Co.; antiozonants, such as "NBC", a nickel dibutyldithiocarbamate, available from DuPont; liquid rubbers such as "VISTANEX LMMH" polyisobutylene rubber; and ultraviolet light inhibitors, such as "IRGANOX 1010" and "TINUVIN P", available from Ciba-Geigy Corp.

Polyvinyl ether pressure sensitive adhesives are generally blends of homopolymers of vinyl methyl ether, vinyl ethyl ether or vinyl iso-butyl ether, or blends of homopolymers of vinyl ethers and copolymers of vinyl ethers and acrylates to achieve desired pressure sensitive properties. Depending on the degree of polymerization, homopolymers may be viscous oils, tacky soft resins or rubber-like substances. Polyvinyl ethers used as raw materials in polyvinyl ether adhesives include polymers based on: vinyl methyl ether such as "LUTANOL M 40", available from BASF, and "GANTREZ M 574" and "GANTREZ 555", available from ISP Technologies, Inc.; vinyl ethyl ether such as "LUTANOL A 25", "LUTANOL A 50" and "LUTANOL A 100"; vinyl isobutyl ether such as "LUTANOL I30", "LUTANOL I60", "LUTANOL IC", "LUTANOL I60D" and "LUTANOL I 65D"; methacrylate/vinyl isobutyl ether/acrylic acid such as "ACRONAL 550 D", available from BASF. Antioxidants useful to stabilize the polyvinylether pressure sensitive adhesive include, for example, "IONOX 30" available from Shell, "IRGANOX 1010" available from Ciba-Geigy, and antioxidant "ZKF" available from Bayer Leverkusen. Other materials can be added for special purposes as described in BASF literature including tackifiers, plasticizers and pigments.

Acrylic pressure sensitive adhesives generally have a glass transition temperature of about −20° C. or less and may comprise from 100 to 80 weight percent of a $C_3$-$C_{12}$ alkyl ester component such as, for example, isooctyl acrylate, 2-ethylhexyl acrylate and n-butyl acrylate and from 0 to 20 weight percent of a polar component such as, for example, acrylic acid, methacrylic acid, ethylene-vinyl acetate units, N-vinylpyrrolidone, and styrene macromer. Generally, the acrylic pressure sensitive adhesives comprise from 0 to 20 weight percent of acrylic acid and from 100 to 80 weight percent of isooctyl acrylate. The acrylic pressure sensitive adhesives may be self-tacky or tackified. Useful tackifiers for acrylics are rosin esters such as "FORAL 85", available from Hercules, Inc., aromatic resins such as "PICCOTEX LC-55WK", aliphatic resins such as "PICCOTAC 95", available from Hercules, Inc., and terpene resins such as α-pinene and ß-pinene, available as "PICCOLYTE A-115" and "ZONAREZ B-100" from Arizona Chemical Co. Other materials can be added for special purposes, including hydrogenated butyl rubber, pigments, and curing agents to vulcanize the adhesive partially.

Poly-α-olefin pressure sensitive adhesives, also called a poly(1-alkene) pressure sensitive adhesives, generally comprise either a substantially uncrosslinked polymer or an uncrosslinked polymer that may have radiation activatable functional groups grafted thereon as described in U.S. Pat. No. 5,209,971 (Babu, et al). The poly-α-olefin polymer may be self tacky and/or include one or more tackifying materials. If uncrosslinked, the inherent viscosity of the polymer is generally between about 0.7 and 5.0 dL/g as measured by ASTM D 2857-93, "Standard Practice for Dilute Solution Viscosity of Polymers". In addition, the polymer generally is predominantly amorphous. Useful poly-α-olefin polymers include, for example, $C_3$-$C_{18}$ poly(1-alkene) polymers, generally $C_5$-$C_{12}$ α-olefins and copolymers of those with $C_3$ or $C_6$-$C_8$ and copolymers of those with $C_3$. Tackifying materials are typically resins that are miscible in the poly-α-olefin polymer. The total amount of tackifying resin in the poly-α-olefin polymer ranges from 0 to 150 parts by weight per 100 parts of the poly-α-olefin polymer depending on the specific application. Useful tackifying resins include resins derived by polymerization of $C_5$ to $C_9$ unsaturated hydrocarbon monomers, polyterpenes, synthetic polyterpenes and the like. Examples of such commercially available resins based on a $C_5$ olefin fraction of this type are "WINGTACK 95" and "WINGTACK 15" tackifying resins available from Goodyear Tire and Rubber Co. Other hydrocarbon resins include "REGALREZ 1078" and "REGALREZ 1126" available from Hercules Chemical Co., and "ARKON P115" available from Arakawa Chemical Co. Other materials can be added for special purposes, including antioxidants, fillers, pigments, and radiation activated crosslinking agents.

Silicone pressure sensitive adhesives comprise two major components, a polymer or gum, and a tackifying resin. The polymer is typically a high molecular weight polydimethylsiloxane or polydimethyldiphenylsiloxane, that contains residual silanol functionality (SiOH) on the ends of the polymer chain, or a block copolymer comprising polydiorganosiloxane soft segments and urea or oxamide terminated hard segments. The tackifying resin is generally a three-dimensional silicate structure that is endcapped with trimethylsiloxy groups (OSiMe$_3$) and also contains some residual silanol functionality. Examples of tackifying resins include SR 545, from General Electric Co., Silicone Resins Division, Waterford, N.Y., and MQD-32-2 from Shin-Etsu Silicones of America, Inc., Torrance, Calif. Manufacture of typical silicone pressure sensitive adhesives is described in U.S. Pat. No. 2,736,721 (Dexter). Manufacture of silicone urea block copolymer pressure sensitive adhesive is described in U.S. Pat. No. 5,214,119 (Leir, et al). Other materials can be added for special purposes, including pigments, plasticizers, and fillers. Fillers are typically used in amounts from 0 parts to 10 parts per 100 parts of silicone pressure sensitive adhesive. Examples of fillers that can be used include zinc oxide, silica, carbon black, pigments, metal powders and calcium carbonate. One particularly suitable class or siloxane-containing pressure sensitive adhesives are those with oxamide terminated hard segments such as those described in U.S. Pat. No. 7,981,995 (Hays) and U.S. Pat. No. 7,371,464 (Sherman).

Polyurethane and polyurea pressure sensitive adhesives useful in this disclosure include, for example, those disclosed in WO 00/75210 (Kinning et al.) and in U.S. Pat. No. 3,718,712 (Tushaus); U.S. Pat. No. 3,437,622 (Dahl); and U.S. Pat. No. 5,591,820 (Kydonieus et al.).

Particularly useful pressure sensitive adhesives are based on at least one poly(meth)acrylate (i.e., a (meth)acrylic pressure sensitive adhesive). Particularly desirable poly (meth)acrylates are derived from: (A) at least one monoethylenically unsaturated alkyl (meth) acrylate monomer (i.e., alkyl acrylate and alkyl methacrylate monomer); and (B) at least one monoethylenically unsaturated free-radically copolymerizable reinforcing monomer. The reinforcing monomer has a homopolymer glass transition temperature (Tg) higher than that of the alkyl (meth)acrylate monomer and is one that increases the glass transition temperature and cohesive strength of the resultant copolymer. Monomers A and B are chosen such that a copolymer formed from them is extrudable and capable of forming fibers. Herein, "copolymer" refers to polymers containing two or more different monomers, including terpolymers, tetrapolymers, etc.

Generally, the monomers used in preparing the pressure sensitive adhesive component of the fibers of the present invention include: (A) a monoethylenically unsaturated alkyl (meth)acrylate monomer that, when homopolymerized, generally has a glass transition temperature (Tg) of no greater than about 0° C.; and (B) a monoethylenically unsaturated free-radically copolymerizable reinforcing monomer that, when homopolymerized, generally has a glass transition temperature of at least about 10° C. The glass transition temperatures of the copolymers of monomers A and B can be measured by differential scanning calorimetry, but more typically the Tg is calculated using the well-known Fox equation utilizing the homopolymer Tg values supplied by the monomer supplier.

Monomer A, which is a monoethylenically unsaturated alkyl acrylate or methacrylate (i.e., (meth)acrylic acid ester), contributes to the flexibility and tack of the copolymer of the adhesive component of the fibers. Generally, monomer A has a homopolymer Tg of no greater than about 0° C. Typically, the alkyl group of the (meth)acrylate has an average of about 4 to about 20 carbon atoms, and more generally, an average of about 4 to about 14 carbon atoms. The alkyl group can optionally contain oxygen atoms in the chain thereby forming ethers or alkoxy ethers, for example. Examples of monomer A include, but are not limited to, 2-methylbutyl acrylate, isooctyl acrylate, lauryl acrylate, 4-methyl-2-pentyl acrylate, isoamyl acrylate, sec-butyl acrylate, n-butyl acrylate, n-hexyl acrylate, 2-ethylhexyl acrylate, n-octyl acrylate, n-decyl acrylate, isodecyl acrylate, isodecyl methacrylate, and isononyl acrylate. Other examples include, but are not limited to, poly-ethoxylated or -propoxylated methoxy (meth)acrylates such as acrylates of CARBOWAX (commercially available from Union Carbide) and NK ester AM90G (commercially available from Shin Nakamura Chemical, Ltd., Japan). Particularly suitable monoethylenically unsaturated (meth)acrylates that can be used as monomer A include isooctyl acrylate, 2-ethyl-hexyl acrylate, and n-butyl acrylate. Combinations of various monomers categorized as an A monomer can be used to make the copolymer used in making the fibers of the present invention.

Monomer B, which is a monoethylenically unsaturated free-radically copolymerizable reinforcing monomer, increases the glass transition temperature and cohesive strength of the copolymer. Generally, monomer B has a homopolymer Tg of at least about 10° C. Typically, monomer B is a reinforcing (meth)acrylic monomer, including an acrylic acid, a methacrylic acid, an acrylamide, or a (meth) acrylate. Examples of monomer B include, but are not limited to, acrylamides, such as acrylamide, methacrylamide, N-methyl acrylamide, N-ethyl acrylamide, N-hydroxyethyl acrylamide, diacetone acrylamide, N,N-dimethyl acrylamide, N, N-diethyl acrylamide, N-ethyl-N-aminoethyl acrylamide, N-ethyl-N-hydroxyethyl acrylamide, N,N-dihydroxyethyl acrylamide, t-butyl acrylamide, N,N-dimethylaminoethyl acrylamide, and N-octyl acrylamide. Other examples of monomer B include itaconic acid, crotonic acid, maleic acid, fumaric acid, 2,2-(diethoxy)ethyl acrylate, 2-hydroxyethyl acrylate or methacrylate, 3-hydroxypropyl acrylate or methacrylate, methyl methacrylate, isobornyl acrylate, 2-(phenoxy)ethyl acrylate or methacrylate, biphenylyl acrylate, t-butylphenyl acrylate, cyclohexyl acrylate, dimethyladamantyl acrylate, 2-naphthyl acrylate, phenyl acrylate, N-vinyl formamide, N-vinyl acetamide, N-vinyl pyrrolidone, and N-vinyl caprolactam. Preferred reinforcing acrylic monomers that can be used as monomer B include acrylic acid and acrylamide. Combinations of various reinforcing monoethylenically unsaturated monomers categorized as a B monomer can be used to make the copolymer used in making the fibers of the present invention.

Generally, the acrylate copolymer is formulated to have a resultant Tg of less than about 25° C. and more typically, less than about 0° C. Such acrylate copolymers typically include about 60 parts to about 98 parts per hundred of at least one monomer A and about 2 parts to about 40 parts per hundred of at least one monomer B. In some embodiments, the acrylate copolymers have about 85 parts to about 98 parts per hundred or at least one monomer A and about 2 parts to about 15 parts of at least one monomer B.

A crosslinking agent can be used if so desired to build the molecular weight and the strength of the copolymer of the adhesive. Typically, the crosslinking agent is one that is copolymerized with monomers A and B. The crosslinking agent may produce chemical crosslinks (e.g., covalent bonds or ionic bonds). Alternatively, it may produce thermal reversible physical crosslinks that result, for example, from the formation of reinforcing domains due to phase separation of hard segments (i.e., those having a Tg higher than room temperature, preferably higher than 70° C.) and/or acid/base interactions (i.e., those involving functional groups within the same polymer or between polymers or between a polymer and an additive). Preferred crosslinking occurs through the use of macromers, such as the styrene macromers of U.S. Pat. No. 4,554,324 (Husman), or polymeric ionic crosslinking as described in WO 99/42536. Suitable crosslinking agents are also disclosed in U.S. Pat. No. 4,737,559 (Kellen), U.S. Pat. No. 5,506,279 (Babu et al.), and U.S. Pat. No. 6,083,856 (Joseph et al.).

In some embodiments, the supporting layer comprises a multi-layer construction. A wide range of multi-layer constructions are suitable. The multi-layer construction may or may not include at least one layer of pressure sensitive adhesive as described above. A particularly suitable multi-layer construction is a transfer tape. Dual-sided tapes, also called "transfer tapes" are adhesive tapes that have adhesive on both exposed surfaces. In some transfer tapes, the exposed surfaces are simply the two surfaces of a single adhesive layer. Other transfer tapes are multi-layer transfer tapes with at least two adhesive layers that may be the same or different, and in some instances intervening layers that may not be adhesive layers. For example, a multi-layer transfer tape may be a 3-layer construction with a first adhesive layer, a middle layer, and a second adhesive layer. The middle layer can provide handling and/or tear strength or other desirable properties. In some embodiments of the sheet articles of this disclosure, the transfer tape comprises a three-layer construction comprising a first pressure sensitive adhesive layer, a second pressure sensitive adhesive layer, and a layer between the first pressure sensitive adhesive layer and the second pressure adhesive layer.

In the present sheet articles, transfer tapes are particularly suitable support layers because they are free-standing articles and can be readily laminated to substrates. In the current disclosure, the electrically conductive particles can be placed on the second major surface of the substrate, and a transfer tape can be laminated to the substrate such that the first major surface of the transfer tape contacts the second major surface of the substrate. In this process, during the lamination of the transfer tape at least some of the electrically conductive particles protrude through the second major surface of the transfer tape. Typically, at least one point of the shaped particles protrudes from the first major surface of the supporting layer by 50-1,000 micrometers.

In embodiments where the substrate is an electrically conductive substrate, the support layer can be either a monolayer of adhesive or a multi-layer transfer tape. In embodiments where the substrate is not an electrically conductive substrate, the supporting substrate includes an electrically conductive layer. In some embodiments, a transfer tape is used as the supporting layer and the center layer of the transfer tape is an electrically conductive layer.

The above described sheet articles can be used to form the dry electrodes described herein. A number of different embodiments of the dry electrodes are described. The embodiments formed from the sheet articles described above can be classified into two general electrode constructions. The first general construction includes an electrically conductive substrate, a discontinuous layer of electrically conductive particles, a support layer, and an electrical connector. The second general electrode construction is related to the first general construction, and includes an electrically conductive layer, a discontinuous layer of electrically conductive particles, and an electrical connector. Each of these constructions is described in detail below.

In some embodiments of the first construction, the dry electrode comprises an electrically conductive substrate with a first major surface and a second major surface, a discontinuous layer of electrically conductive particles where at least some of the electrically conductive particles are in contact with the second major surface of the conductive substrate, and a supporting layer with a first major surface and a second major surface, where the first major surface of the supporting layer is in contact with the second major surface of the electrically conductive substrate, and an electrical connector in electrical contact with the second major surface of the electrically conductive substrate. The electrically conductive particles comprise shaped particles with at least one point. In this embodiment, the supporting layer envelopes the electrically conductive particles such that the at least one point of at least one of the electrically conductive particles protrudes from the second major surface of the supporting layer.

The dry electrode includes an electrically conductive substrate. The electrically conductive substrate serves as a support layer for the electrically conductive particles described below. A wide range of electrically conductive substrates are suitable, and have been described above. In some embodiments the electrically conductive substrate comprises a film layer, such as a polymeric film layer, with a conductive coating. Examples of polymeric films include films comprising one or more polymers such as cellulose acetate butyrate; cellulose acetate propionate; cellulose triacetate; poly(meth)acrylates such as polymethyl methacrylate; polyesters such as polyethylene terephthalate, and polyethylene naphthalate; copolymers or blends based on naphthalene dicarboxylic acids; polyether sulfones; polyurethanes; polycarbonates; polyvinyl chloride; syndiotactic polystyrene; cyclic olefin copolymers; and polyolefins including polyethylene and polypropylene such as cast and biaxially oriented polypropylene. The film may comprise single or multiple layers, such as polyethylene-coated polyethylene terephthalate. A wide range of conductive coatings are suitable such as thin coatings of metal, metal grids or continuous coatings of conductive carbon.

The dry electrode also includes a discontinuous layer of electrically conductive particles. By discontinuous layer it is meant that the layer includes discrete particles that are not all in contact with each other. The electrically conductive particles are described in detail above.

The first general electrode construction includes a supporting layer. The supporting layer has a first major surface and a second major surface. The first major surface of the supporting layer is in contact with the second major surface of the electrically conductive substrate. In this embodiment, the supporting layer envelopes the electrically conductive particles such that the at least one point of at least one of the electrically conductive particles protrudes from the second major surface of the supporting layer. Generally, the supporting layer has a thickness of from 25-500 micrometers, in some embodiments 50-150 micrometers.

Suitable supporting layers are described in detail above. In the present dry electrodes, transfer tapes are particularly suitable support layers because they are free-standing articles and can be readily laminated to substrates. In the current disclosure, the electrically conductive particles can be placed on the second major surface of the electrically conductive substrate, and a transfer tape can be laminated to the electrically conductive substrate such that the first major surface of the transfer tape contacts the second major surface of the electrically conductive substrate. In this process, during the lamination of the transfer tape at least some of the electrically conductive particles protrude through the second major surface of the transfer tape. Typically, at least one point of the shaped particles protrudes from the first major surface of the supporting layer by 50-1,000 micrometers.

The dry electrode also includes an electrical connector. The electrical connector is in electrical contact with the second major surface of the electrically conductive substrate, and protrudes from the electrically conductive substrate.

A wide range of electrical connectors are suitable for use in the dry electrodes of the present disclosure. Essentially any electrical connector that is suitable for use with wet or dry electrodes are suitable for use in the current dry electrodes. Examples include the connector studs described in U.S. Pat. No. 6,415,170 (Loutis et al.). The studs have an electrode plate portion located on one side of the substrate of the dry electrode for electrical connection to the skin of the wearer of the dry electrode through the electrically conductive substrate and the electrically conductive particles. On the other side of the electrical connector is a head portion to which an electrical device can be attached. The head portion can take a wide variety of shapes and sizes.

Also disclosed herein is a second general electrode construction. The second general electrode construction is related to the first general construction, and includes an electrically conductive layer, a discontinuous layer of electrically conductive particles, and an electrical connector. This embodiment is similar to the first general electrode construction described above, but in this embodiment the electrically conductive substrate and support layer of first general construction are combined in a single element, the electrically conductive layer, rather than being two distinct elements. This general electrode construction can likewise be prepared from the sheet articles described above. Suitable sheet articles for forming these dry electrodes are those in which the supporting layer comprises a conductive layer and the substrate comprises a non-conductive substrate.

In some embodiments of the second general electrode construction, the dry electrode comprises an electrically conductive layer with a first major surface and a second major surface, a discontinuous layer of electrically conductive particles, and an electrical connector. The electrically conductive layer may be a single layer but, as is described below, typically includes other non-conductive layers and thus is a multi-layer construction. In this embodiment, at least some of the electrically conductive particles comprise shaped particles with at least one point and the electrically conductive layer envelopes the electrically conductive particles such that the at least one point of at least one of the electrically conductive particles protrudes from the second major surface of the electrically conductive layer. The electrical connector is in electrical contact with the second major surface of the electrically conductive layer, the electrically conductive particles, or a combination thereof, and the electrical connector protrudes from the first major surface of the electrically conductive layer.

A wide variety of materials may be used as the electrically conductive layer, as long as the layer is electrically conductive and is able to envelop the discontinuous layer of electrically conductive particles. Typically, the electrically conductive layer has a thickness of from 25-500 micrometers.

In some embodiments, the electrically conductive layer comprises a multi-layer construction. Particularly suitable multi-layer constructions are transfer tapes. Transfer tapes have been described above. An example of a suitable transfer tape for use as the electrically conductive layer is a three-layer construction comprising a first pressure sensitive adhesive layer, a second pressure sensitive adhesive layer, and a conductive interlayer between the first pressure sensitive adhesive layer and the second pressure adhesive layer. In this embodiment, the electrically conductive particles are embedded within the second pressure sensitive adhesive layer and are in electrical contact with the electrically conductive interlayer of the transfer tape, and the electrical connector is embedded in the first pressure sensitive adhesive layer and in electrical contact with the electrically conductive interlayer of the transfer tape.

The particles and electrical connector suitable for the second general construction of the electrode are the same as the particles and electrical connector described above for use in the first general construction of the electrode. As with the first general electrode, at least one point of the shaped particles protrudes from the second major surface of the electrically conductive layer by 50-1,000 micrometers.

Also disclosed herein are dry electrodes that can be prepared with electrically conductive particles but are not prepared from sheet articles, rather discrete dry electrodes can be prepared directly. In these embodiments, a dry electrode can be formed by adhering a discontinuous layer of electrically conductive particles to the electrode plate portion of an electrical connector. The electrically conductive particles and electrical connectors are described above.

This embodiment can be prepared by contacting and adhering electrically conductive particles to the electrode plate portion of an electrical connector. A wide variety of techniques and materials can be used to adhere the electrically conductive particles to the electrical connector as long as electrical connectivity is maintained between the electrically conductive particles and the electrical connector. An electrically conductive adhesive can be used to adhere the electrically conductive particles to the electrical connector. The electrode plate of the electrical connector can be coated with an electrically conductive adhesive to form a continuous or discontinuous layer of electrically conductive adhesive on the electrode plate portion. The electrically conductive particles can then be contacted to the coated electrode plate portion. In other embodiments, the electrically conductive particles can be adhered to the electrical connector by soldering, or similar techniques such as heating of the electrical connector to a temperature that causes the electrically conductive coating of the electrically conductive particles to soften and form an electrically conductive interaction between the electrically conductive particles and the electrical connector. As mentioned above, while this embodiment describes the formation of a discrete dry electrode, these techniques can also be used to form an array of discrete dry electrodes. Formation of an array of discrete dry electrodes permits mass production of these electrodes.

It may be desirable to add additional elements to this discrete construction to form the dry electrode. For example, since the electrical connectors are typically relatively small, a substrate layer can be attached to the construction to provide a larger electrode that is easier to handle. Additionally, a supporting layer as described above can be added to the construction. As with previously described constructions, at least one point of at least one conductive particle protrudes through the supporting layer. These additional elements provide support and ease of handling of the dry electrode.

Also disclosed herein are methods of preparing dry electrodes. A wide variety of methods are suitable. As described above, in some embodiments the method involves preparing a sheet article and using this sheet article to prepare the dry electrode. These methods vary depending upon whether the prepared dry electrode is the first or the second general electrode construction. Additionally, discrete dry electrodes can be prepared directly without first preparing a sheet article.

In some embodiments, the method of forming a dry electrode comprises forming a precursor sheet article, where the precursor sheet article includes a general method, which can be made into the electrode by adding an electrical connector. The method is general for preparing both general electrode constructions. The general method of preparing an electrode comprises providing a substrate with a first major surface and a second major surface, providing electrically conductive particles, contacting at least one electrically conductive particle with the second major surface of the substrate such that at least one point protrudes from the second major surface of the substrate, providing a layer of supporting material with a first major surface and a second major surface, contacting the first major surface of the layer of supporting material to the second major surface of the substrate and the electrically conductive particles, such that the at least one point protrudes through the second major surface of the supporting material layer.

The electrically conductive particles comprise shaped particles with at least one point, as described in detail above. In methods where the dry electrode comprises a first general construction, the substrate comprises an electrically conductive substrate. Electrically conductive substrates have been described in detail above. The method further comprises contacting an electrical connector to the electrically conductive substrate to form electrical connectivity. The electrically conductive substrate may be a multi-layer construction. In some embodiments, the electrically conductive substrate comprises a two-layer construction with an electrically conductive layer forming the second major surface of the substrate and a non-conductive layer forming the first major surface of the substrate.

In these embodiments, the supporting material comprises the support layer described above. In some embodiments, the supporting material layer comprises a layer of pressure sensitive adhesive. The pressure sensitive adhesive can be supplied as a liquid or solution and coated to the electrically conductive substrate layer that contains a discontinuous layer of electrically conductive particles. The pressure sensitive adhesive layer can then be dried if it is dissolved in a solvent, allowed to solidify if supplied in a molten form, or cured if provided as an uncured composition. The pressure sensitive adhesive can also be provided as a preformed pressure sensitive adhesive layer that is laminated to the electrically conductive substrate layer that contains a discontinuous layer of electrically conductive particles. However the pressure sensitive adhesive is applied to the electrically conductive substrate layer that contains a discontinuous layer of electrically conductive particles, at least some of the points of the particles of the discontinuous layer protrude through the pressure sensitive adhesive layer.

Additionally, as described above, the supporting material layer may comprise a multilayer construction. An example of a suitable multilayer construction is a transfer tape, where the transfer tape comprises a three-layer construction comprising a first pressure sensitive adhesive layer, a second pressure sensitive adhesive layer, and a layer between the first pressure sensitive adhesive layer and the second pressure adhesive layer. The transfer tape in these embodiments may further comprise a release liner in contact with second pressure sensitive adhesive layer. The methods that include a transfer tape or similar type of support layer include contacting the first major surface of the layer of supporting material to the second major surface of the substrate and the electrically conductive particles. In embodiments where the supporting layer is a three layer transfer tape this step comprises laminating the first pressure sensitive adhesive layer to the second major surface of the substrate and the electrically conductive particles, and applying pressure to the release liner of the laminated transfer tape to press the point of the electrically conductive particle through the transfer tape, and removing the release liner to expose the second pressure sensitive adhesive and the protruding point of the electrically conductive particle.

The supporting layer, regardless of its composition or how it is formed has a suitable thickness to permit at least one point of the electrically conductive particle to protrude through the second major surface of the supporting layer. Typically, the supporting layer has a thickness of 10-500 micrometers.

Other embodiments of the method of this disclosure involve preparing a dry electrode of the second general construction. These embodiments also involve using a preformed sheet article, but the elements of the sheet article are different than the elements in the sheet article precursors described above. In these embodiments, the substrate comprises a non-conductive substrate and the layer of supporting material comprises the electrically conductive layer described above. The non-conductive substrate may be a removable substrate. By removable substrate it is meant that the substrate is not incorporated into the final dry electrode, but is used as a carrier on which to place the conductive particles. Examples of removable substrates include release liners, as described above. In other embodiments, the non-conductive substrate in not a removable substrate but remains as part of the final article. Typically, the non-conductive substrate comprises a polymeric film. Examples of suitable polymeric films include films comprising one or more polymers such as cellulose acetate butyrate; cellulose acetate propionate; cellulose triacetate; poly(meth)acrylates such as polymethyl methacrylate; polyesters such as polyethylene terephthalate, and polyethylene naphthalate; copolymers or blends based on naphthalene dicarboxylic acids; polyether sulfones; polyurethanes; polycarbonates; polyvinyl chloride; syndiotactic polystyrene; cyclic olefin copolymers; and polyolefins including polyethylene and polypropylene such as cast and biaxially oriented polypropylene. The film may comprise single or multiple layers, such as polyethylene-coated polyethylene terephthalate.

As mentioned above, the layer of supporting material comprises the electrically conductive layer. Suitable electrically conductive layers are described in detail above. The electrically conductive layer may be a single layer or it may be a multi-layer construction. Formation of the electrically conductive layer can be achieved by lamination of a transfer tape to the second major surface of the substrate and the discontinuous layer of conductive particles. In other embodiments, a curable or flowable material can be coated onto the second major surface of the substrate and the discontinuous layer of conductive particles. This coating can be cured if the coating is curable or allowed to cool and harden in cases where the coating is flowable, with the proviso that upon curing or cooling the coating is electrically conductive. In some embodiments, the electrically conductive layer comprises a pressure sensitive adhesive, but the electrically conductive layer need not be an adhesive layer. In embodiments where the electrically conductive layer comprises an adhesive, the electrically conductive layer may be an electrically conductive adhesive or it may be multi-layer construction such as a transfer tape that contains a conductive layer.

As with the method for preparing the dry electrode of the first general construction, the method for preparing the dry electrode of the second general construction further comprises contacting an electrical connector to the electrically conductive layer and/or the electrically conductive particles to form electrical connectivity.

The supporting layer, regardless of its composition or how it is formed, has a suitable thickness to permit at least one point of the electrically conductive particle to protrude through the second major surface of the supporting layer. Typically, the supporting layer has a thickness of 10-500 micrometers.

If the substrate is a removable substrate, the removable substrate can be removed prior to or after the electrical connector is contacted to the electrically conductive layer and/or the electrically conductive particles to form electrical connectivity. The surface exposed by removal of the removable substrate can be left as an open surface or, if desired, a different substrate can be adhered to this surface.

The embodiments of this disclosure can be further understood by referring to the Figures.

Figure 1:
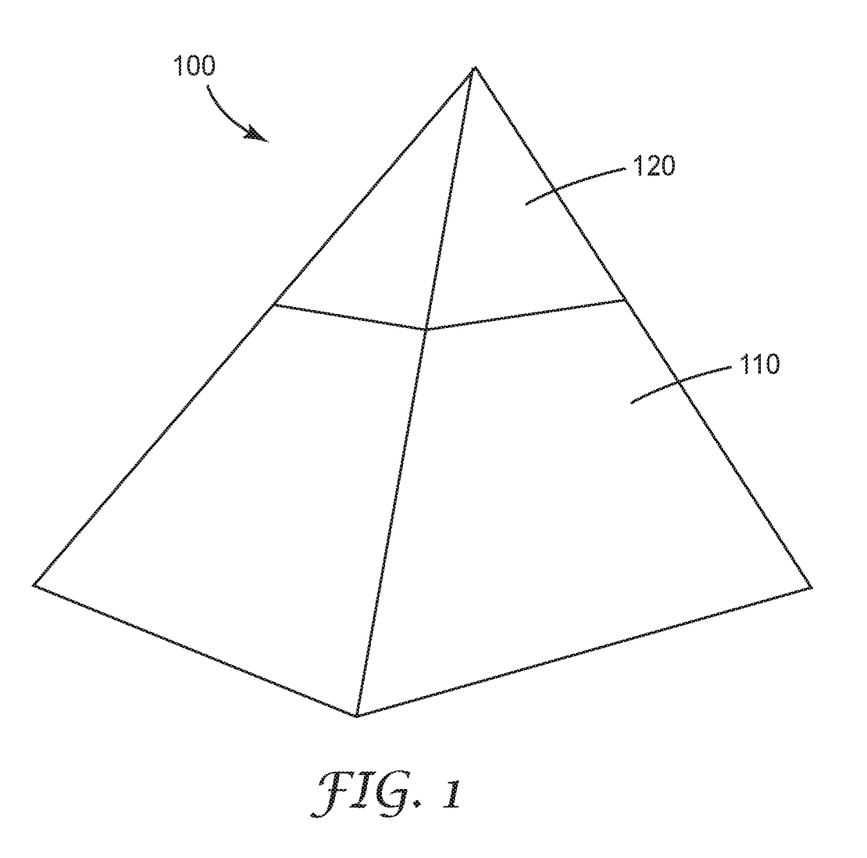
FIG. 1 is a cross sectional view of an embodiment of a conductive particle of the present disclosure.

FIG. 1 is a cross sectional view of an embodiment of a shaped conductive particle of this disclosure. In FIG. 1, shaped conductive particle 100 has conductive coating 110 over the entire particle and secondary conductive coating 120 over just a portion of the particle.

Figure 2:
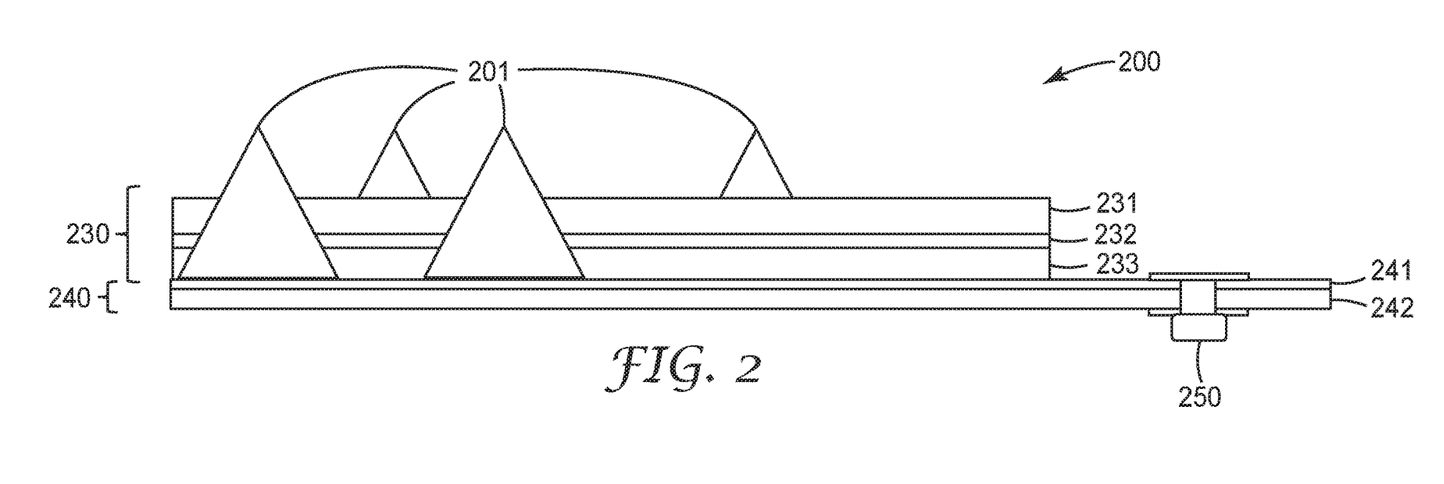
FIG. 2 is a cross sectional view of an embodiment of a dry electrode of the present disclosure.

FIG. 2 shows one embodiment of a dry electrode of this disclosure. In FIG. 2, dry electrode 200 has conductive particles 201, supporting layer 230 which has 3 sublayers 231, 232, 233 where 231 and 233 are adhesive layers and 232 is film layer. Layer 240 is a conductive substrate which includes conductive layer 241 and optional film layer 242. Electrical connector 250 is in electrical contact with the conductive substrate 240.

Figure 3:
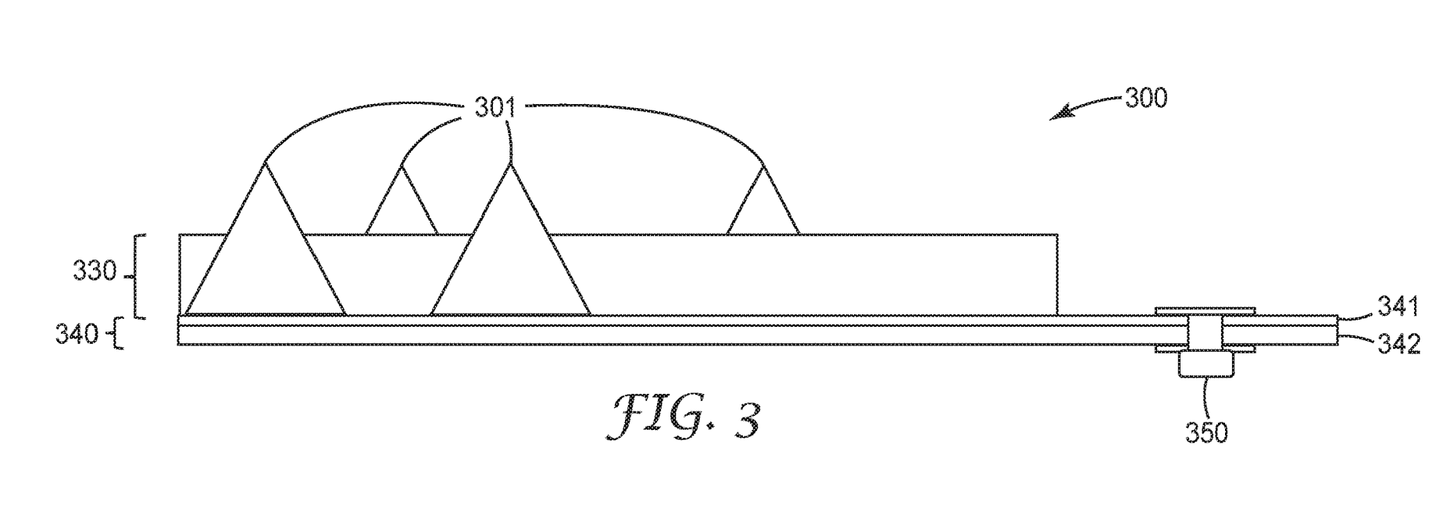
FIG. 3 is a cross sectional view of another embodiment of a dry electrode of the present disclosure.

FIG. 3 is another embodiment of a dry electrode of this disclosure and is similar to the dry electrode shown in FIG. 2. In FIG. 3, dry electrode 300 has conductive particles 301, monolithic supporting layer 330, conductive substrate 340 which includes conductive layer 341 and optional film layer 342, and electrical connector 350.

Figure 4:
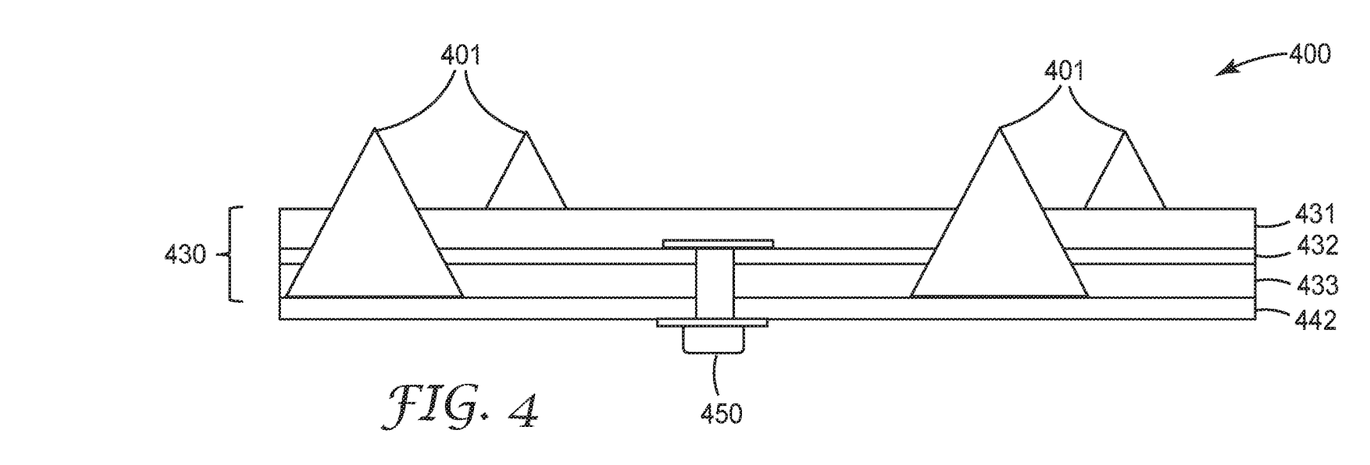
FIG. 4 is a cross sectional view of another embodiment of a dry electrode of the present disclosure.

FIG. 4 is yet another embodiment of a dry electrode of this disclosure. In FIG. 4, dry electrode 400 has conductive particles 401, and supporting layer 430 which has 3 sublayers 431, 432, 433, where 431 and 433 are adhesive layers and 432 is a conductive layer. Layer 442 is a non-conductive substrate layer. Layer 442 is shown as monolithic layer, but could be a multi-layer construction. Electrical connector 450 is in electrical contact with the conductive layer 432.

Figure 5:
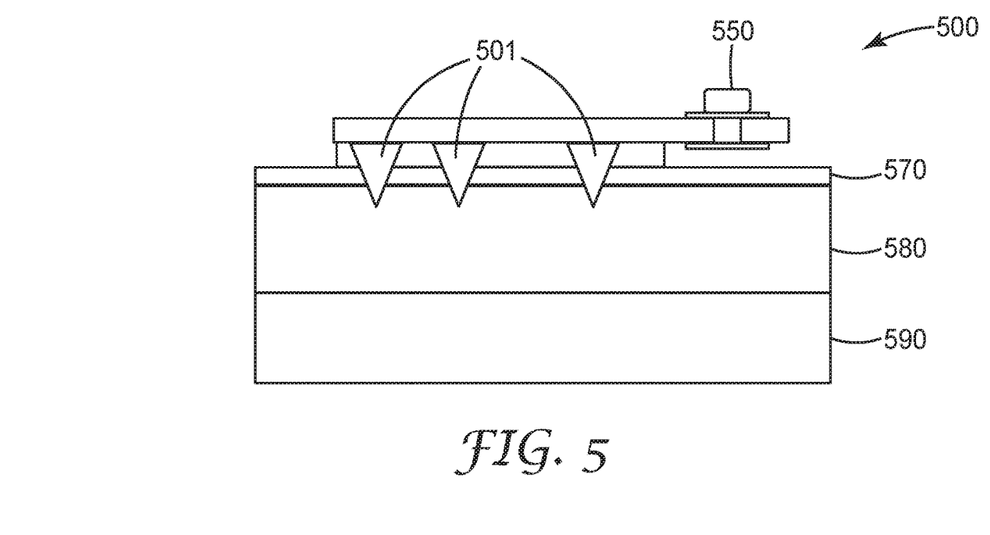
FIG. 5 is a cross sectional view of the use of an embodiment of a dry electrode of this disclosure on human skin.

FIG. 5 shows how the dry electrodes of this disclosure are used, dry electrode 500 has conductive particles 501 that penetrates stratum corneum layer 570 and contacts the epidermis layer 580, but not to the dermis layer 590. Dry electrode 500 can be any of the dry electrodes shown above, with electrical connector 550.

Figure 6:
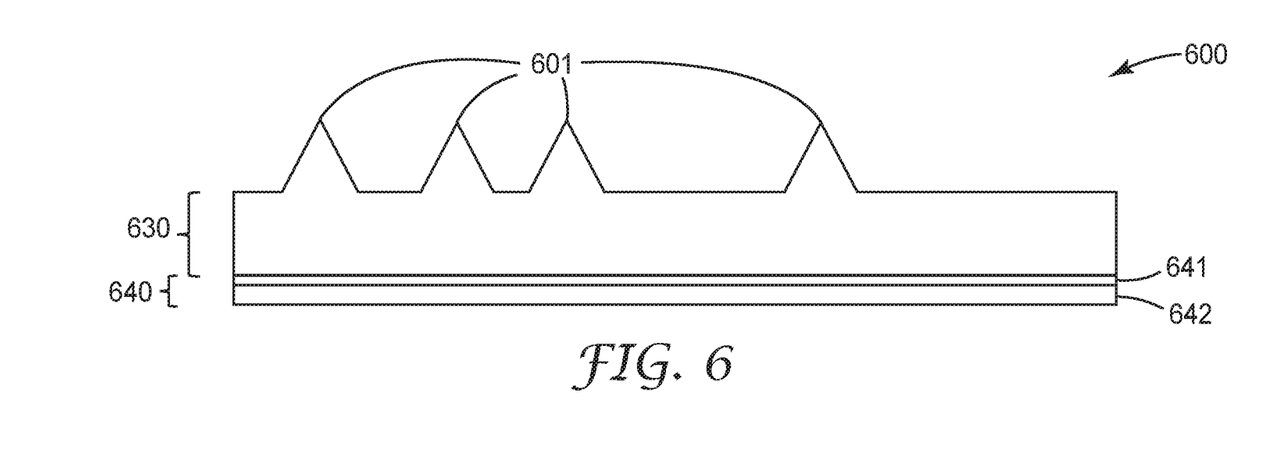
FIG. 6 is a cross sectional view of a sheet article of this disclosure that is capable of forming a dry electrode.

FIG. 6 is an embodiment of a sheet article of this disclosure capable of forming a dry electrode. In FIG. 6, sheet article 600 has conductive particles 601, supporting layer 630, substrate layer 640 which has conductive layer 641 and film layer 642. It will be understood that substrate layer 640 in some embodiments is a non-conductive substrate layer, and can be a monolithic layer or a multi-layer. Also, supporting layer 630 can be a multi-layer construction, and in some embodiments contains a conductive layer.

Figure 7:
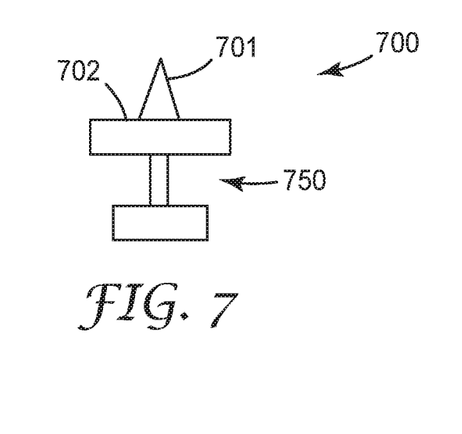
FIG. 7 is a cross sectional view of another embodiment of a dry electrode of the present disclosure.

FIG. 7 is another embodiment of a dry electrode of this disclosure, in this instance a discrete dry electrode. In FIG. 7, dry electrode 700 has conductive particle 701 adhered at surface 702 to electrical connector 750. The surface 702 can be a conductive adhesive layer, a solder connection, etc.

Figure 8:
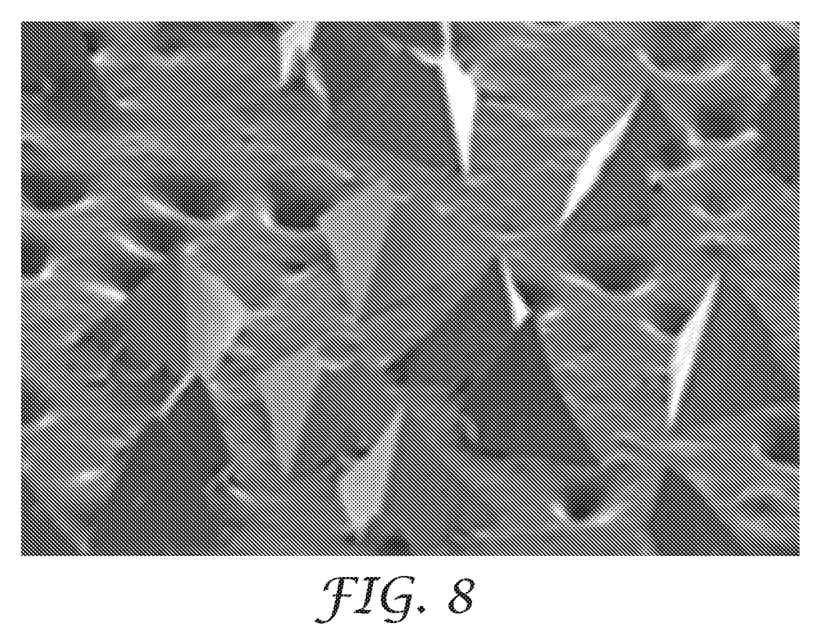
FIG. 8 is a photograph showing shaped particles of this disclosure.

FIG. 8 is a photograph showing shaped conductive particles on a substrate layer.

Figure 9:
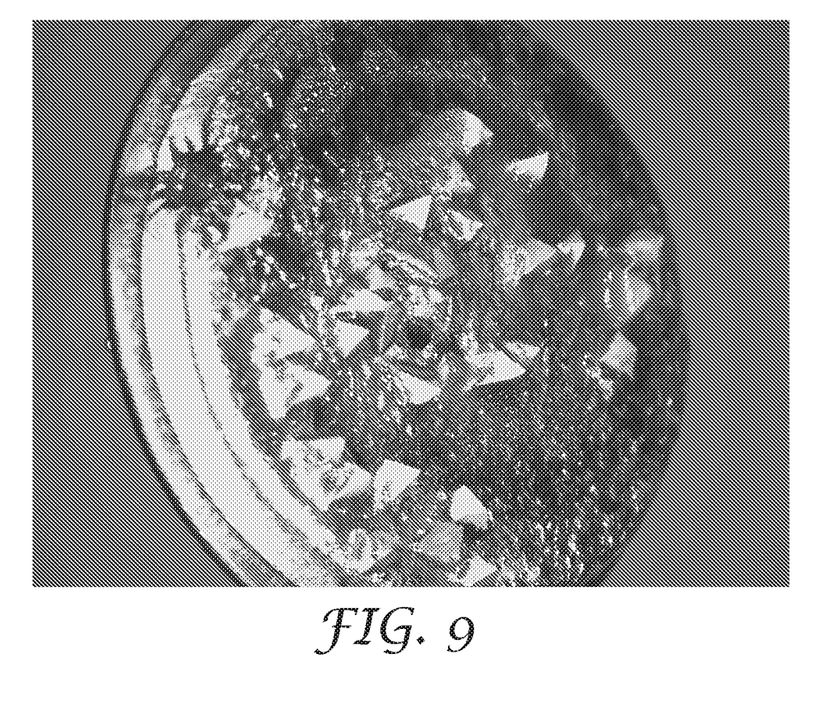
FIG. 9 is a photograph showing the electrode prepared in Example 8.

FIG. 9 is a photograph showing shaped conductive particles on an electrical connector as described by FIG. 7 above and Example 8 below.

EXAMPLES

These examples are merely for illustrative purposes only and are not meant to be limiting on the scope of the appended claims. All parts, percentages, ratios, etc. in the examples and the rest of the specification are by weight, unless noted otherwise. Solvents and other reagents used were obtained from Sigma-Aldrich Chemical Company, St. Louis, MO, unless otherwise noted.

Production of Precision Shaped Grain (PSG) Tetrahedrons

The ceramic tetrahedrons were produced according to the procedures outlined in U.S. Pat. No. 8,142,531. Alpha alumina particles were made from a dispersion of aluminum oxide monohydrate that is gelled, molded to shape, dried to retain the shape, calcined, and then sintered. In this case, a mold having a plurality of regular tetrahedron-shaped polymeric cavities was used to shape the sol-gel, yielding particles with edges approximately 33 mils (0.84 mm) long after sintering.

A sample of boehmite sol-gel was made using the following recipe: aluminum oxide monohydrate powder (1600 parts) having the trade designation DISPERAL (available from CONDEA Chemie GmbH, Hamburg, Germany) was dispersed by high shear mixing into a solution containing water (2400 parts) and 70% aqueous nitric acid (72 parts) for 5 minutes. The resulting sol-gel was aged for at least one hour before coating. The sol-gel was forced into production tooling having tetrahedral mold cavities. The sol-gel was forced into the cavities with a putty knife so that the openings of the production tooling were filled. A mold release agent (0.2% peanut oil in methanol) had been used to coat the production tooling, with about 0.1 mg/in$^2$ of peanut oil applied to the production tooling. The methanol was allowed to evaporate from the production tooling before the sol-gel was coated. The sol-gel coated production tooling was left at room temperature overnight to dry. The precursor tetrahedral-shaped particles were removed from the production tooling by passing it over an ultrasonic horn. The precursor tetrahedral-shaped particles were calcined at approximately 650° C. and then saturated with a mixed nitrate solution of the following concentration (reported as oxides): 1.8% each of MgO, $Y_2O_3$, $Nd_2O_3$, and $La_2O_3$. The excess nitrate solution was removed and the saturated precursor tetrahedral-shaped particles with openings were allowed to dry, after which the particles were again calcined at 650° C. and sintered at approximately 1400° C. Both the calcining and sintering was performed using rotary tube kilns. The tetrahedral particles formed by this process had edges approximately 33 mils (0.84 mm) long after sintering.

Preparation of Silver Coated PSG Alumina Particles by Physical Vapor Deposition

Metallizing particles were produced through the use of physical vapor deposition (PVD) including magnetron sputtering. The PVD method of metallizing particles is disclosed in for example, U.S. Pat. Nos. 4,612,242 and 7,727,931. The apparatus used in the following preparation of silver coated PSG particles is described in published U.S. Patent Application No. 2014/0363554.

Forty cubic centimeters (41.45 g) of the PSG tetrahedrons prepared above were loaded into the particle agitator inside the vacuum chamber apparatus. The vacuum chamber was pumped down to $2\times10^{-05}$ torr, and then 125 sccm (standard cubic centimeter per minute) of argon gas was admitted. The sputtering process was initiated using a Ag (3" round) target. The sputter power was 0.75 kW and the process pressure was 13 millitorr. The PSG tetrahedrons were tumbled at 14 rpm during the sputter process. After 2 hours, the sputter process was stopped, the chamber was vented with air and the silver-coated tetrahedrons were removed from the particle agitator. The density of silver coated tetrahedral particles was 4.1 g/cc and the estimated Ag weight percent was 3.8.

Conversion of Silver to Silver Chloride

A fraction of the Ag on the particle surfaces was converted to AgCl by a redox reaction in an aqueous solution of 0.03% $NaO_2Cl$ and 2% KCl. A target AgCl conversion ratio was selected, and tetrahedrons having 10-50% AgCl based on the initial Ag content were produced. The mass of Ag in each sample was calculated using the mass of the coated tetrahedrons to be converted and the coated tetrahedron's Ag mass fraction. Each mole of $NaO_2Cl$ converts 4 moles of Ag to AgCl. The coated tetrahedrons were added to the solution and intermittently agitated for approximately 30 minutes. The tetrahedrons were then filtered, washed with water 3 times and subsequently dried.

Assembling Dry Electrodes

The backing of a 3M RED DOT ELECTRODE 9650 (available from 3M Company, St. Paul, MN) was used as the conductive substrate for each dry example electrode. This backing is polyester film coated with a continuous layer of conductive carbon. Stripes of silver, 2 cm wide, are printed on top of the carbon separated by 0.9 cm stripes of uncoated carbon.

To fabricate a dry electrode, Ag/AgCl coated tetrahedrons were dropped from a height of roughly 1 cm and settled randomly on the conductive substrate. The number of tetrahedrons per electrode is provided in Table 1 and is reported as "Number of Points".

A 2.8 mil (71 micrometers) thick tackified acrylic transfer adhesive (LONG TERM WEAR ADHESIVE 4075, available from 3M Company, St. Paul, MN) was laminated to the nonwoven urethane backing of LONGTERM WEAR TAPE 4077 (also available from 3M Company, St. Paul, MN). A strip of this construction 0.75" (19 mm) wide was laminated over the particles distributed on the conductive substrate after the liner covering the 4077 adhesive was removed. A hand-held rubber roller (1.5" (3.8 cm) diameter, 1.88" (4.8 cm) length) was used to force the tops of the tetrahedrons through the adhesive layers, nonwoven backing and paper release liner on the 4075 transfer adhesive by passing over the strip 3-5 times with approximately 20 pounds pressure.

The electrode backing was cut parallel to the adhesive tape and 5 mm from its edge. The resultant strip was cut perpendicular to its length at 0.75" (19 mm) intervals, yielding square electrodes with 5 mm tabs of exposed conductive substrate.

Examples

Examples 1-3 were produced using tetrahedrons with a side length of 33 mils (0.84 mm). The tetrahedrons were coated with approximately 3.8% by weight silver, and 30% of the silver was converted to silver chloride. Each dry electrode measured 0.75 inch (1.9 cm) by 0.75 inch (1.9 cm) and had a 5 mm wide conductive connecting tab on one side to facilitate electrical connection. Samples were made with a range of tetrahedral particle densities and the number of particle points penetrating the release liner were counted under 10× magnification. Electrodes with the same number of points were paired and a range of point densities tested.

The release liners were removed from matched pairs of electrodes. The pairs of electrodes were placed 4 inches (10.2 cm) apart on a male volunteer's leg and pressed in place with moderate finger pressure for approximately one second. Impedance between the electrodes was measured using an EIM-105-10 Hz Prep-Check Electrode Impedance Meter (General Devices, Inc., Indianapolis, Ind). Fresh sites were used for the application of each electrode. For each electrode pair, the distance between centers was kept constant at 4 inches (10.2 cm). Table 1 presents the results from pairs of these electrodes having different numbers of tetrahedrons per electrode. "Number of Points" in Table 1 indicates the number of points (tetrahedrons) on each electrode in the pair. As a control, RED DOT 2670 hydrogel-based electrodes (3M Company, St. Paul, MN) were used and are referred to as Comparative Example 1.

Comparative Example 1 shows the typical performance of electrodes comprising hydrogels, with a high initial impedance that decreases as the stratum corneum absorbs moisture from the hydrogel. The low initial impedance of Examples 1-3, relative to the initial impedance of Comparative Example 1, indicates the points have penetrated the stratum corneum, bypassing the high impedance that would be attributed to the stratum corneum's low moisture content. (The stratum corneum typically contains 5-20% moisture. The epidermis, into which the tetrahedrons penetrate, contains 60-70% moisture.)

A large number of penetrators is not required to achieve a relatively low impedance as evidenced by 8 points being nearly as effective as 30.

The stability of the impedance values for Examples 1-3 over the first three hours is an improvement relative to the changing impedance of Comparative Example 1. A changing impedance, as the stratum corneum absorbs an increasing amount of moisture from the hydrogel, could impact the measurements being made with the electrode.

TABLE 1

Electrode impedance measurements (kOhms, measured with AC meter at 10 Hz) over time with electrodes having different numbers of Ag/AgCl-coated tetrahedral points per electrode.

| | Number of Points | Initial | 5 Minutes | 60 Minutes | 120 Minutes | 180 Minutes | 48 Hours |
|---|---|---|---|---|---|---|---|
| Example 1 | 8 | 50 | 56 | 39 | 56 | 55 | |
| Example 2 | 23 | 30 | 38 | 34 | 32 | 33 | |
| Example 3 | 31 | 26 | 32 | 35 | 37 | 32 | 33 |
| Comparative Example 1 RED DOT 2670 | | 160 | 87 | 72 | 27 | 22 | |

Examples 4-7 were prepared and tested on human subjects by the method described above, but with varying levels of silver to silver chloride conversion. The data reported in Table 2 shows that tetrahedrons with AgCl percentages of 10-50% produced electrodes with acceptable performance.

TABLE 2

Electrode impedance (kOhms) measurements over time with electrodes having different percentages of the Ag coating on the tetrahedrons converted to AgCl.

| Example | Percent of Ag converted to AgCl | Number of Points | Initial | 5 Minutes | 60 Minutes | 120 Minutes |
|---|---|---|---|---|---|---|
| 4 | 10 | 14 | 57 | 55 | 50 | 51 |
| 5 | 20 | 14 | 42 | 41 | 40 | 38 |
| 6 | 30 | 16 | 36 | 40 | 40 | 33 |
| 7 | 50 | 17 | 38 | 39 | 34 | 34 |

Example 8

A thin layer of soldering paste (CHIP QUIK Solder Paste No-Clean Sn42/Bi57.6/Ag0.4 from CHIP QUIK) was spread on the skin contact side of an electrical connector similar to those shown, for example, as element 250, 350, 450, or 550 in the FIGS. Silver coated tetrahedrons with 30% AgCl conversion prepared as described above were placed onto the soldering paste. This coated electrical connector was then heated above the cure temperature of the soldering paste and allowed to cool, producing an electrode comprising an electrical connector with silver/silver chloride coated tetrahedrons affixed to its surface, which is illustrated schematically in FIG. 7 and a photograph of the electrode is shown in FIG. 9.

These electrodes were tested on the skin of a human subject and their electrical performance compared to electrodes that comprised untreated electrical connectors. Pairs of electrodes were placed approximately 4 inches (10 cm) apart on the skin, and in the case of the electrodes comprising electrical connectors with silver/silver chloride coated tetrahedrons affixed to their surface, the tetrahedrons were in contact with the skin. Skin impedance was tested using an EIM-105-10 Hz Prep-Check Electrode Impedance Meter. For the electrodes comprising untreated electrical connectors, impedance readings were above the detection limit of the instrument (>200 kOhms). For the electrodes comprising electrical connectors with silver/silver chloride coated tetrahedrons affixed to their surface, the impedance reading was approximately 151 kOhms after 10 seconds in contact with the skin. The electrodes comprising electrical connectors having silver/silver chloride coated tetrahedrons soldered to the skin contact side showed improved electrical performance.

What is claimed is:

1. An electrode comprising:
   an electrically conductive substrate with a first major surface and a second major surface;
   a discontinuous layer of electrically conductive particles wherein at least some of the electrically conductive particles are in contact with the second major surface of the conductive substrate, wherein the electrically conductive particles comprise shaped particles with at least one point for penetrating the stratum corneum and epidermis layers of skin, and wherein the electrically conductive particles comprise ceramic particles including a conductive coating;
   a supporting layer with a first major surface and a second major surface, where the first major surface of the supporting layer is in contact with the second major surface of the electrically conductive substrate and the supporting layer envelopes the electrically conductive particles such that the at least one point of at least one of the electrically conductive particles protrudes from the second major surface of the supporting layer; and
   an electrical connector in electrical contact with the second major surface of the electrically conductive substrate, and protruding from the electrically conductive substrate.

2. The electrode of claim 1, wherein the electrically conductive particles comprise non-compressive shaped particles wherein at least one dimension of the shaped particles is 175-1,500 micrometers.

3. The electrode of claim 1, wherein the supporting layer comprises a layer of pressure sensitive adhesive.

4. The electrode of claim 1, wherein the supporting layer comprises a transfer tape, wherein the transfer tape comprises a three-layer construction comprising a first pressure sensitive adhesive layer, a second pressure sensitive adhesive layer, and a layer between the first pressure sensitive adhesive layer and the second pressure adhesive layer.

5. The electrode of claim 1, wherein the at least point of the shaped particles protrudes from the first major surface of the supporting layer by 50-1,000 micrometers.

6. The electrode of claim 1, wherein the conductive coating is a first conductive coating, and wherein the electrically conductive particles further comprise a second conductive coating.

7. The electrode of claim 6, wherein the second conductive coating covers only a portion of the first conductive coating.

8. The electrode of claim 1, wherein the support layer comprises a first layer, a second layer layered onto the first layer, and a third layer layered onto the second layer.

9. The electrode of claim 8, wherein the first layer and third layer comprise adhesive layers, and wherein the second layer comprises a film layer.

10. The electrode of claim 1, wherein the electrically conductive substrate comprises a conductive layer and a polymeric film layer.

11. The electrode of claim 1, wherein the electrode lacks an electrolyte gel.

12. The electrode of claim 7, wherein the second conductive coating covers the at least one point for penetrating the stratum corneum and epidermis layer of skin.

* * * * *